US00PP23748P2

(12) United States Plant Patent
Ichie

(10) Patent No.: US PP23,748 P2
(45) Date of Patent: Jul. 16, 2013

(54) ***HYDRANGEA* PLANT NAMED 'TINKERBELL'**

(50) Latin Name: *Hydrangea macrophylla*
Varietal Denomination: Tinkerbell

(76) Inventor: Toyokazu Ichie, Kakegawa (JP)

( * ) Notice: Subject to any disclaimer, the term of this patent is extended or adjusted under 35 U.S.C. 154(b) by 34 days.

(21) Appl. No.: 13/374,987

(22) Filed: Jan. 26, 2012

(51) Int. Cl.
*A01H 5/00* (2006.01)

(52) U.S. Cl.
USPC ..... Plt./250

(58) Field of Classification Search
USPC ..... Plt./250
See application file for complete search history.

*Primary Examiner* — Kent L Bell
(74) *Attorney, Agent, or Firm* — Penny J. Aguirre

(57) ABSTRACT

A new cultivar of *Hydrangea macrophylla* named 'Tinkerbell', that is characterized by its remontant (re-blooming) habit, blooming from May until frost, its lacecap type inflorescences with double sterile flowers surrounding a mass of fertile flowers, its flowers that are pink in color when grown with a soil PH of 7 or above, and its sterile flowers with sepals that have white margins.

2 Drawing Sheets

Botanical classification: *Hydrangea macrophylla.*
Varietal denomination: 'Tinkerbell'.

BACKGROUND OF THE INVENTION

The present invention relates to a new and distinct cultivar of *Hydrangea macrophylla* and will be referred to hereafter by its cultivar name, 'Tinkerbell'. 'Tinkerbell' represents a new modified lace cap type *Hydrangea*, a deciduous shrub grown for landscape use and for use as a potted plant.

'Tinkerbell' originated as a seedling that arose from seed planted from a controlled pollination by the Inventor in Shizuoka Prefecture Kakegawa, Japan in 2003. The parents were unnamed plants of *Hydrangea macrophylla* from the Inventor's breeding line; the female parent with designation no. H4-62 and the male parent with designation no. H4-50. The new *Hydrangea* was selected as a single unique plant in 2010.

Asexual reproduction of the new cultivar was first accomplished by the Inventor using softwood stem cuttings in Kakegawa, Japan in 2010. The characteristics of this cultivar have been determined to be stable and are reproduced true to type in successive generations.

SUMMARY OF THE INVENTION

The following traits have been repeatedly observed and represent the characteristics of the new cultivar. These attributes in combination distinguish 'Tinkerbell' as a unique cultivar of *Hydrangea macrophylla.*

1. 'Tinkerbell' exhibits a remontant (re-blooming) habit, blooming from May until frost.
2. 'Tinkerbell' exhibits lacecap type inflorescences with double sterile flowers surrounding a mass of fertile flowers.
3. 'Tinkerbell' exhibits flowers that are pink in color when grown with a soil PH of 7 or above.
4. 'Tinkerbell' exhibits double sterile flowers with sepals that have white margins.

'Tinkerbell' differs from its female parent, H4-62, in having a remontant blooming habit and in having a more compact plant habit. 'Tinkerbell' differs from its male parent, H4-50, in having double sterile flowers. 'Tinkerbell' can be most closely compared to the cultivars 'Frau Reiko' (U.S. Plant Pat. No. 9,500) and 'Dancing Butterflies Two' (U.S. Plant patent application Ser. No. 13/317,953). 'Tinkerbell' differs from 'Frau Reiko' in having a remontant blooming habit, a more compact plant habit and in having double sterile flowers. 'Tinkerbell' differs from 'Dancing Butterflies Improved' in having double sterile flowers.

BRIEF DESCRIPTION OF THE DRAWINGS

The accompanying colored photographs illustrate the overall appearance and distinct characteristics of the new *Hydrangea* as grown in a greenhouse in Kakegawa, Japan. The photographs were taken of one year-old plants of 'Tinkerbell' as grown in a 23-cm container.

The photograph in FIG. 1 provides a close-up view of an inflorescence of 'Tinkerbell' when grown in alkaline soils (without aluminum) and the photograph in FIG. 2 provides a close-up view of the inflorescences of 'Tinkerbell' when grown in acidic soils (with aluminum).

Figure 1:
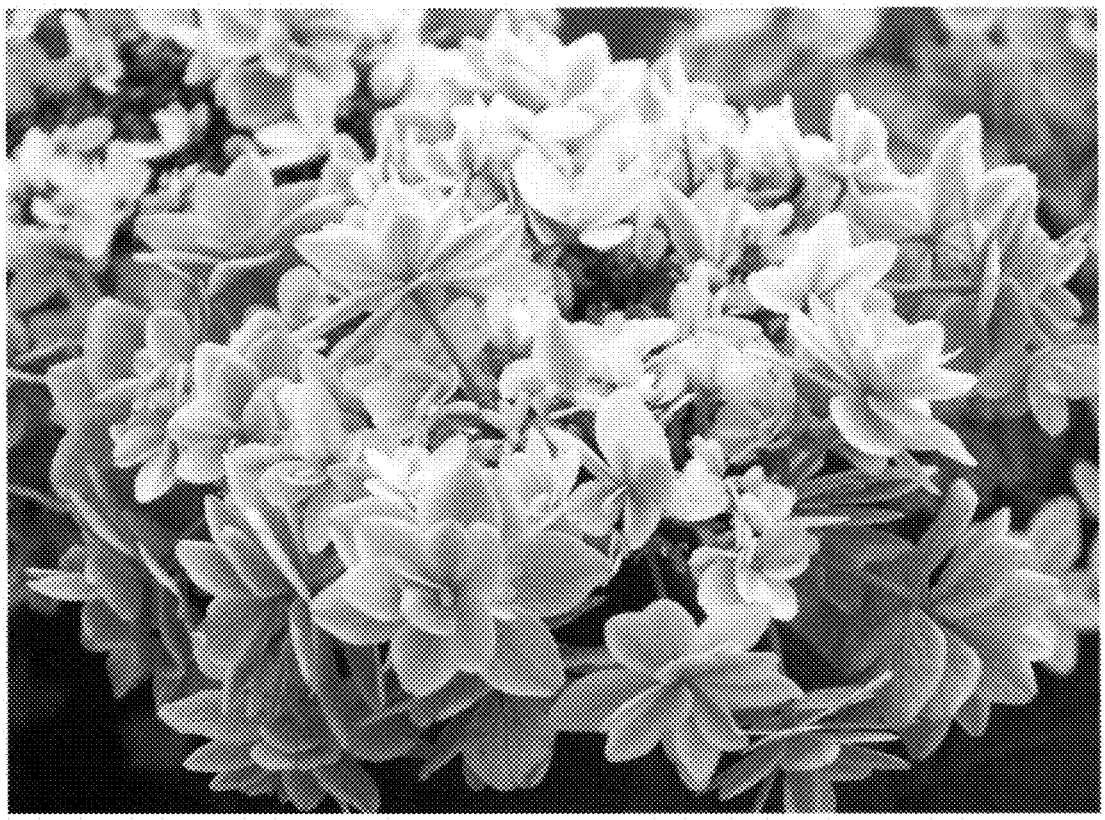
Figure 2:
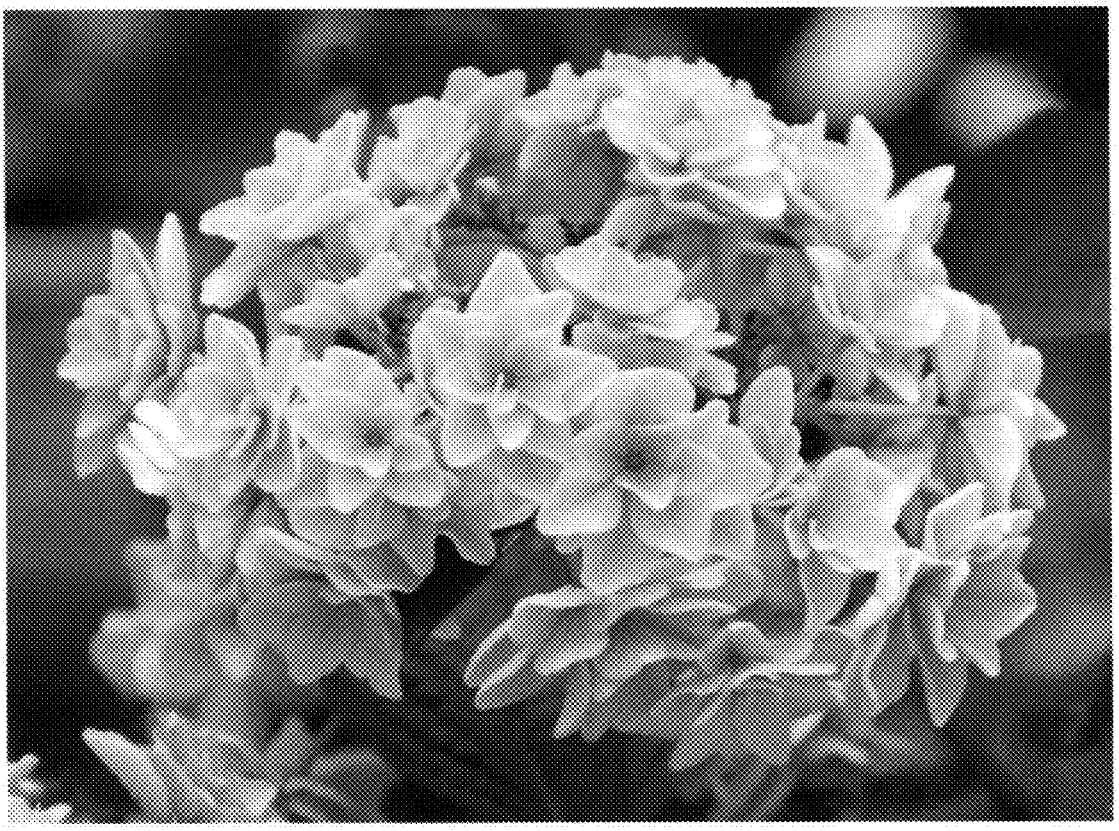

The colors in the photographs may differ slightly from the color values cited in the detailed botanical description, which accurately describe the colors of the new *Hydrangea.*

BOTANICAL DESCRIPTION OF THE PLANT

The following is a detailed description of one year-old plants of 'Tinkerbell' as grown in a greenhouse in 23-cm containers in Kakegawa Japan. The detailed flower color data was taken from plants growing both under acidic conditions (with aluminum) and alkaline conditions (without aluminum) when differences exist. Phenotypic differences may be observed with variations in environmental, climatic, and cultural conditions. The color determination is in accordance with The 2001 R.H.S. Colour Chart of The Royal Horticultural Society, London, England, except where general color terms of ordinary dictionary significance are used.

General description:

*Blooming period.*—Re-blooming from May until frost in Kakegawa, Japan, blooming will continue in winter with extended daylight.

*Plant type.*—Deciduous shrub, modified lace cap type *Hydrangea.*

*Plant habit.*—Broadly upright, well-branched.

*Height and spread.*—Reaches about 60 cm in height and 80 cm in width.

*Hardiness.*—At least in U.S.D.A. Zones 5 to 9.

*Diseases resistance.*—Has been observed to be tolerant to powdery mildew.

*Root description.*—Fine.

Growth and propagation:

*Propagation.*—Softwood stem cuttings, an average of 10 months from propagation to flowering plant.

*Growth rate and vigor.*—Moderate.

Stem description:

*Stem shape.*—Round, solid.

*Stem strength.*—Strong.

*Stem color.*—Young growth; close to 144C, mature growth; 198C.

*Stem size.*—Average of 45 cm in length (excluding inflorescence), average of 8 mm in diameter.

*Stem surface.*—Glabrous and glossy.

*Internode length.*—Average of 12 cm.

*Branching.*—Heavy branched, an average of 10 lateral branches on a one year-old plant and an average of 30 stems a year once established in the landscape.

Foliage description:

*Leaf shape.*—Broadly oval.

*Leaf arrangement.*—Opposite.

*Leaf division.*—Simple.

*Leaf number.*—Average of 16 (8 pairs) per lateral branch.

*Leaf base.*—Cuneate.

*Leaf apex.*—Acute to acuminate.

*Leaf margins.*—Serrate.

*Leaf venation.*—Pinnate, upper and lower surface; 136D.

*Leaf size.*—An average of 12 cm in length and 8 cm in width.

*Leaf attachment.*—Petiolate.

*Leaf surface.*—Smooth, moderately glossy.

*Leaf color.*—Young foliage upper surface; 131B, young foliage lower surface; 131C, mature foliage upper surface; 131B, mature foliage lower surface; 131C.

*Petioles.*—Average of 3 cm in length and 5 mm in diameter, 139C in color, glabrous surface.

Inflorescence description:

*Inflorescence type.*—Terminal compound corymb, modified lacecap in form comprised of a center region of fertile flowers surrounded by an outer ring of double sterile flowers.

*Lastingness of inflorescence.*—Persistent but color is retained for about 3 weeks.

*Inflorescence number.*—One per lateral or sublateral stem if pinched.

*Inflorescence size.*—Average of 10.5 cm in height and 10 cm in width.

*Flower number.*—Average of 15 sterile flowers and 100 fertile flowers per panicle.

*Flower fragrance.*—None.

*Flower aspect.*—Double sterile and fertile flowers arranged on terminal lacecap-type panicles, flowers face upright or outward.

*Flower size.*—Sterile flowers; average of 2 cm in diameter and 1 cm in depth, fertile flowers; average of 1 mm in diameter and 4 mm in depth.

*Flower type.*—Rotate.

*Flower buds.*—Sterile flowers; average of 6 mm in length and 4.5 mm in width prior to opening, ovate in shape, 62B in color prior to opening, fertile flowers; average of 4 mm in width and diameter, obovate to rounded in shape, 62B in color.

*Peduncles.*—Moderately strong, average of 5 cm in length and 4 mm in width, average angle of 10° from vertical, 144B in color.

*Pedicels.*—Held at a 25° angle from vertical, average of 2 cm in length and 2 mm in width on sterile flowers and an average of 4 mm in length and 1 mm in width on fertile flowers, 66B in color and glabrous surface on all flowers.

*Petals.*—Fertile flowers; average of 5, rotate in arrangement, ovate to lanceolate in shape, entire margin, acute apex, truncate base, average of 4 mm in length and 2 mm in width, surface is smooth and dull on both surfaces, color of both surfaces is 62A (without aluminum) and 91B (with aluminum) and fading to 144C, sterile flowers; closed into eye under most conditions, an average of 6, eye is an average of 2 mm in diameter and depth, color 62A (without aluminum) and 91B (with aluminum), glabrous surface.

*Sepals.*—Sterile flowers; average of 14, broadly ovate in shape, up to 1 cm in length and 8 mm in width, broadly acute apex, cuneate to rounded base, glabrous surface on upper and lower surface, entire margins, color 62A with margins 69D (without aluminum) and 91B with margins 92D (with aluminum), fertile flowers; average of 14, ovate to lanceolate in shape, serrated margin, obtuse and retuse apex, attenuate base, average of 3 mm in length and 2 mm in width, surface is smooth and slightly glossy on both surfaces, color of upper and lower surface 144D.

Reproductive organs: (Fertile flowers).

*Stamens.*—Average of 10, anther is oblong in shape, 1 mm in length and 80B in color, filament is 5 mm in length, pollen is scarce in quantity and 156B in color.

*Pistils.*—Average of 4, average of 1 mm in length, stigma is rounded and 79A in color, style is an average of 1 mm in length and 79A in color, ovary is 145B in color.

*Fruit and seed.*—Has not been observed under the conditions tested to date.

It is claimed:

1. A new and distinct cultivar of *Hydrangea* plant named 'Tinkerbell' substantially as herein illustrated and described.

* * * * *